United States Patent [19]
Wright

[11] Patent Number: 5,752,286
[45] Date of Patent: May 19, 1998

[54] CLEANING AND STORAGE SYSTEM FOR A BODY CAVITY ASPIRATOR INSTRUMENT

[76] Inventor: Clifford A. Wright, 12737 Isocoma St., San Diego, Calif. 92129

[21] Appl. No.: 575,988

[22] Filed: Dec. 21, 1995

[51] Int. Cl.⁶ .................................................. B08B 3/04
[52] U.S. Cl. ........................... 15/104.92; 15/104.04; 134/169 R; 134/170
[58] Field of Search .................... 15/104.04, 104.92, 15/302; 134/169 R, 170; 206/207, 210

[56] References Cited

U.S. PATENT DOCUMENTS

| | | | |
|---|---|---|---|
| 4,439,884 | 4/1984 | Giorni | 15/104.92 |
| 4,748,007 | 5/1988 | Gaudion et al. | 134/170 |
| 4,813,538 | 3/1989 | Balckman | 206/210 |
| 5,454,131 | 10/1995 | Mackenzie | 15/104.92 |
| 5,471,706 | 12/1995 | Wallock et al. | 15/104.92 |

*Primary Examiner*—Terrence Till
*Attorney, Agent, or Firm*—Jerry R. Potts

[57] ABSTRACT

A new and improved cleaning and storage system for a body cavity aspirator instrument includes a holder having a narrow mouth configuration for receiving an aspirator instrument therein for temporary storage purposes between periods of non-use. An inlet disposed in a base portion and spaced apart from a distal end of the holder permits the admittance of a cleaning agent in a sufficient volume into the base portion of the holder to clean the instrument according to the novel method of cleaning. A wiper cap disposed over the mouth of the holder, helps wipe the instrument of residual fluids when being inserted and removed from the holder. A mounting arrangement permits the holder to be supported from any convenient surface in close proximity to a patient/user.

18 Claims, 2 Drawing Sheets

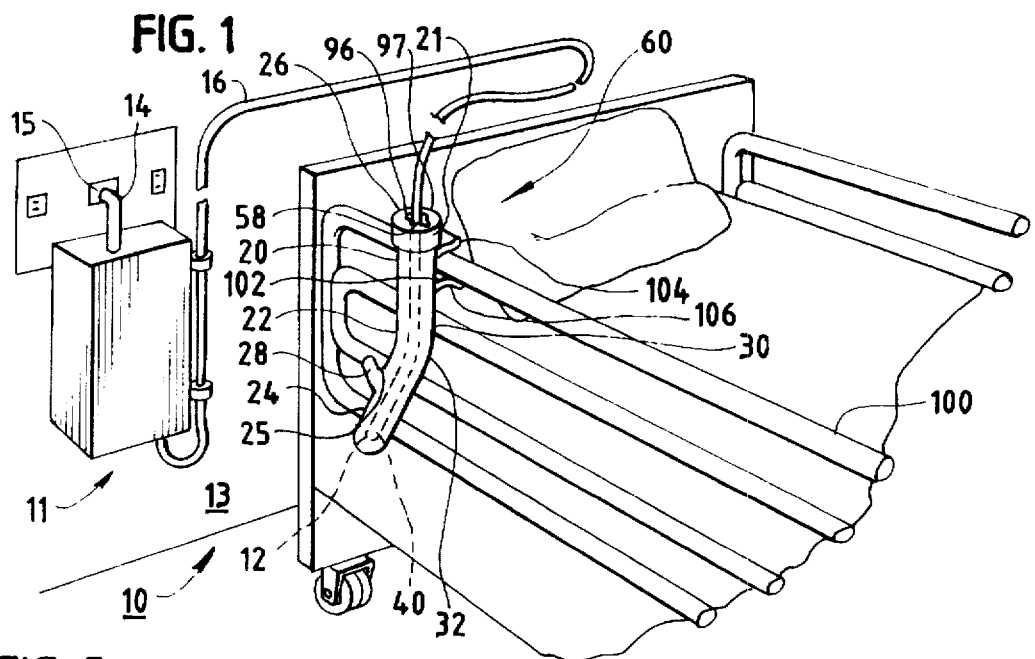
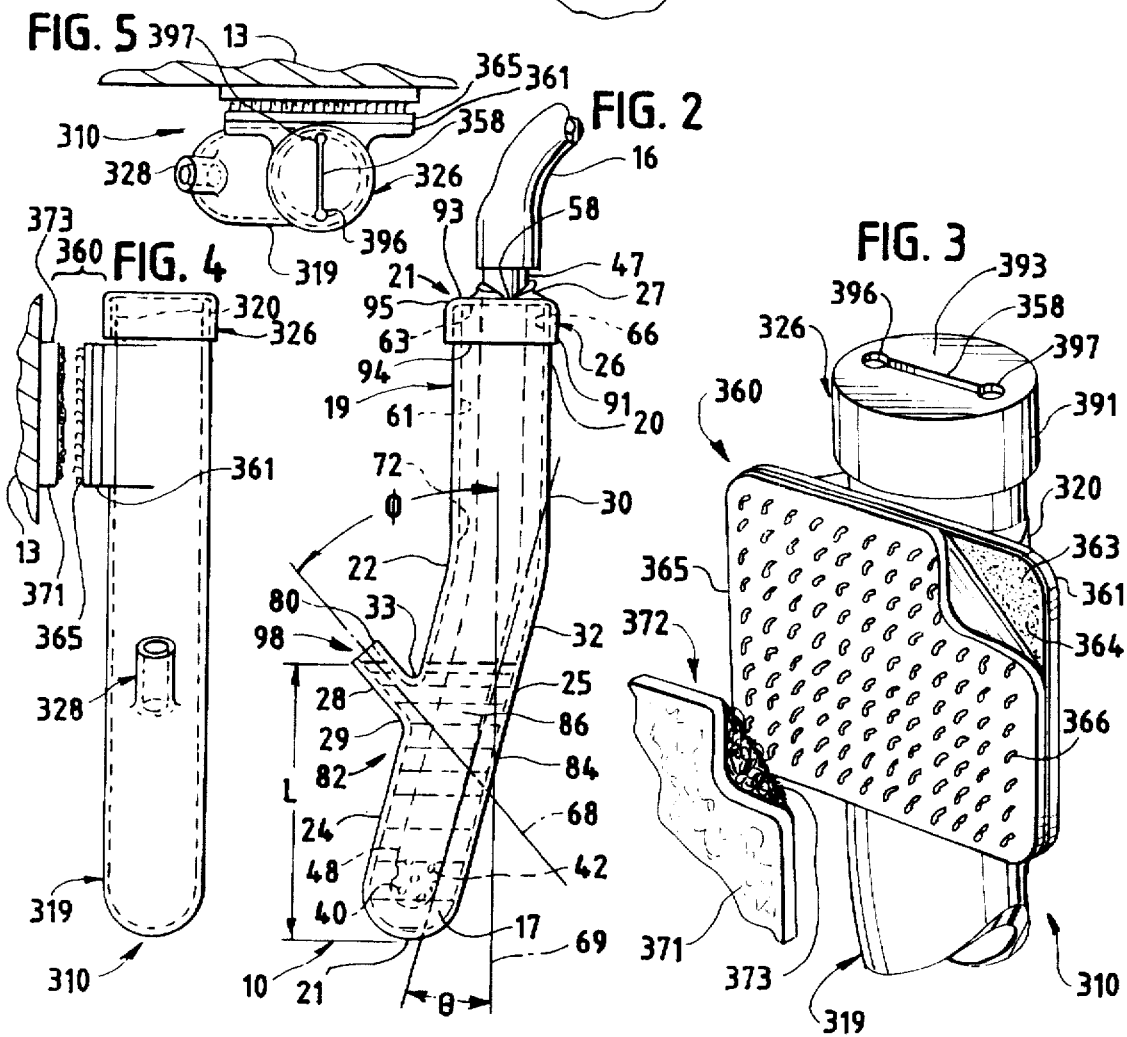

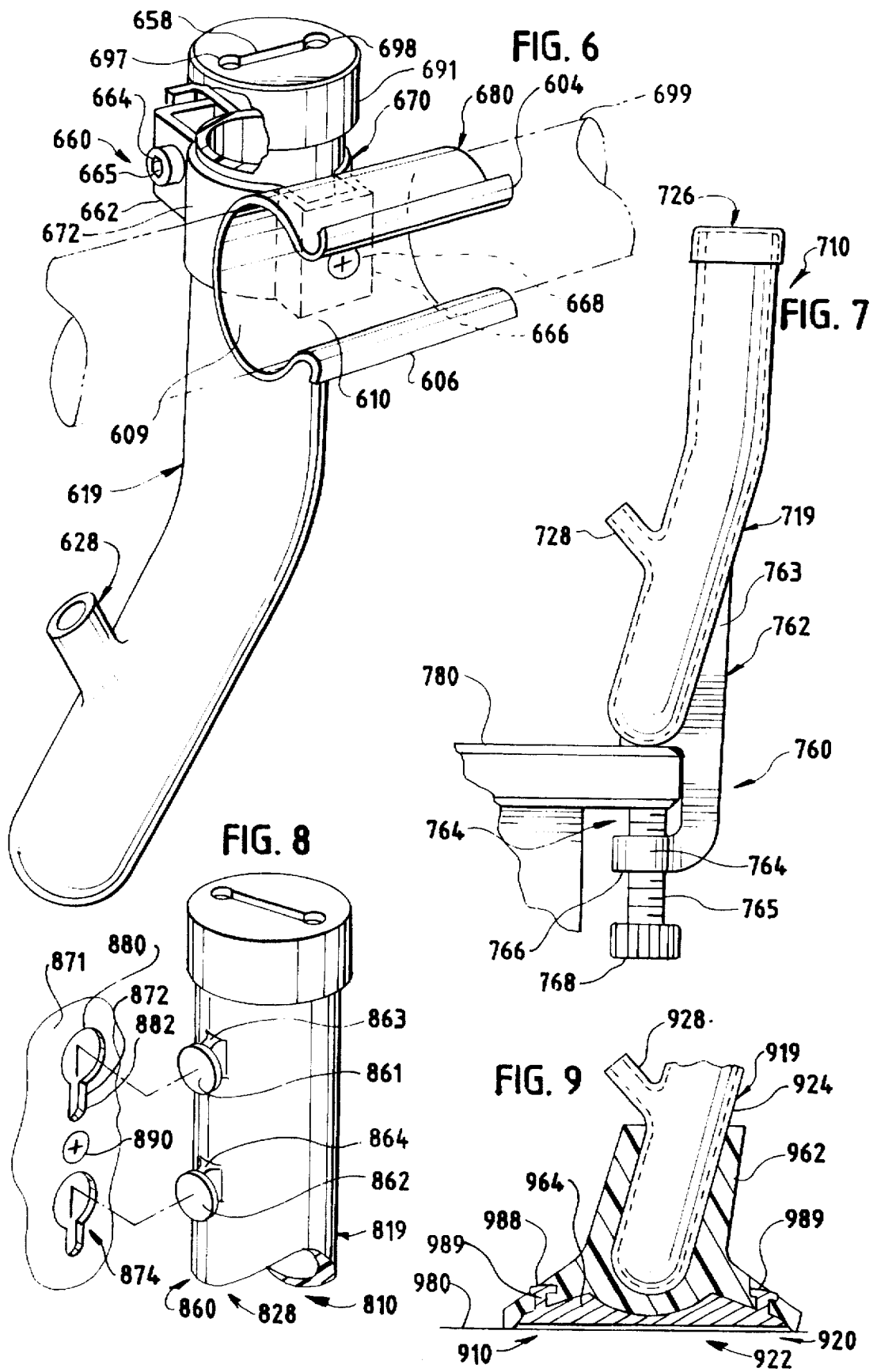

5,752,286

CLEANING AND STORAGE SYSTEM FOR A BODY CAVITY ASPIRATOR INSTRUMENT

TECHNICAL FIELD

The present invention relates in general to a cleaning and storage system for an aspirator instrument. The present invention more particularly relates to a cleaning and storage system for a body cavity aspirator instrument which facilitates the storage of a body cavity aspirator instrument when not in use and which further facilitates the cleaning of the body cavity aspirator instrument prior to its use by a patient.

BACKGROUND ART

For many patient care applications, bodily fluids, such as mucus fluids and meconium fluids, as well as other potentially harmful bodily fluids must be removed from a patient and disposed of in a safe and efficient manner. In this regard, there have been many different types and kinds of aspirator instruments, devices and tools for moving bodily fluids by suction or vacuum processes. For example, reference may be made to the following U.S. Pat. Nos.: 5,333,607; 5,183,467; 5,062,835; 5,038,766; 5,002,534; and 4,921,488, each of said patents being incorporated herein by reference.

As disclosed in the foregoing mentioned patents, various aspirator instruments are configured for removing certain types of bodily fluids from specific body cavities. For example, U.S. Pat. No. 5,183,467 discloses an aspirator instrument which is used to dislodge and remove secretions, mucus and debris from a nasal passageway of a user or patient, while U.S. Pat. No. 5,062,835 discloses an aspirator device which can remove meconium or mucus fluids from a stomach or lung cavity during delivery of an infant.

Aspirator instruments then, are configured in various shapes depending upon their intended use and more specifically depending upon the shape of the body cavity holding the bodily fluids to be removed. For example, U.S. Pat. No. 5,002,534 discloses a very common type of oral aspirator device for removing fluids from the mouth and throat cavities of a user or patient.

Because the removal of mucus fluids from the mouth and throat of patients confined in a primary care facility, such as a hospital facility, is such a common requirement in patient care, most, if not all, primary care facilities are equipped with bedside access control consoles. Such access control consoles provide primary care givers immediate access to gases, monitoring equipment and suction/vacuum/water sources for patient care and treatment.

U.S. Pat. No. 5,002,534 describes in detail the typical use of such an oral aspirator instrument indicating the aspirator instrument is attached to the neck of a user/patient using a cord so that a mouthpiece or Yankauer tip instrument can be easily inserted into the mouth of the patient for drawing mucus and other fluids from the body cavity of the patient.

While such an arrangement may have been satisfactory for some applications, it has proven to be less than satisfactory in that a health care provider when not using the aspirator is compelled to either remove the aspirator instrument from the aspirator or lay the instrument with the vacuum tube attached thereon on the patient or the bed of the patient. Thus, if the instrument has been in use, residual body fluids may contaminate the patient or the bed of the patient creating an unwanted and undesired health risk due to the presence of undesirable bacteria and harmful bodily fluids.

Conversely, if the user desires to maintain a safe, clean environment, the aspirator must be utilized promptly so that the Yankauer instrument can be removed and immediately disposed of or alternately removed and placed in a proper container for cleaning and sterilization purposes.

While such a procedure can be followed for minimizing the creation of unwanted and undesired health risks, it is very expensive and time consuming, particularly, where a patient must have his or her mouth and throat cleared on a regular and short term or elapsed time basis.

Therefore, it would be highly desirable to have a new and improved cleaning and storage system for a body cavity aspirator instrument which would prevent, or at least greatly reduce, the possibility of creating unwanted and undesired health risk due to contaminating a patient or the bed coverings of the patient with undesirable and harmful residual bodily fluids from a used body cavity aspirator instrument.

Another problem associated with prior known aspirator systems when utilized on a regular short elapsed time basis is associated with the accumulation of residual mucus fluids in and on the Yankauer tip when the vacuum or suction is terminated. In this regard, in many aspirator systems, when the body cavity aspirator instrument is removed from the mouth of the patient, the suction operation is substantially diminished permitting any fluids remaining in the body cavity instrument to be trapped within the tip or end of the instrument and tubing connected to the aspirator.

Therefore, it would be highly desirable to have such a new and improved cleaning and storage system for a body cavity aspirator instrument which would eliminate or at least greatly reduce, the possibility of residual bodily fluids being present in the aspirator instrument when the same instrument is used in multiple body fluid removal sessions.

DISCLOSURE OF INVENTION

Therefore, the principal object of the present invention is to provide a new and improved cleaning and storage system for a body cavity aspirator instrument wherein the aspirator instrument is adapted to be used repeatedly by the same patient without creating unwanted and undesired health risks.

Another object of the present invention is to provide such a new and improved cleaning and storage system for a body cavity aspirator instrument wherein the aspirator instrument is adapted to be cleaned and cleared of residual body fluid when the same instrument is temporarily stored and then subsequently utilized for bodily fluid removal purposes.

Briefly, the above and further objects are realized by providing a new and improved cleaning and storage system for a body cavity aspirator instrument wherein an aspirator instrument is stored temporarily for repeated use without creating unwanted and undesired health risks from residual body fluid contamination according to novel holding, cleaning and using methods of the present invention.

The cleaning and storage system for an aspirator instrument includes a holder having a narrow mouth configuration for receiving an aspirator instrument therein for temporary storage purposes between periods of non-use. An inlet disposed in a base portion and spaced apart from a distal end of the holder facilitates cleaning the aspirator instrument of any residual bodily fluids accumulated in and on the aspirator instrument between periods of non-use. In this regard, the inlet permits the admittance of a cleaning agent in a sufficient volume into the base portion of the holder to clean the instrument according to the novel method of cleaning. A wiper cap disposed over the mouth of the holder, helps wipe the instrument of residual fluids when being inserted and removed from the holder. A mounting arrangement permits the holder to be supported from any convenient surface in close proximity to a patient/user.

BRIEF DESCRIPTION OF DRAWINGS

The above mentioned and other objects and features of this invention and the manner of attaining them will become apparent, and the invention itself will be best understood by reference to the following description of the embodiment of the invention in conjunction with the accompanying drawings, wherein:

FIG. 1 is a pictorial view of a cleaning and storage system for a body cavity aspirator instrument, which is constructed in accordance with the present invention and illustrating the temporary storage of such an instrument at the bedside of a health care facility bed;

FIG. 2 is an enlarged partially cross-sectional rear elevational view of an aspirator instrument holder of FIG. 1, illustrating an aspirator instrument partially emersed in a cleaning agent for cleaning purposes;

FIG. 3 is a fragmentary pictorial view of another cleaning and storage system for a body cavity aspirator instrument, which is constructed in accordance with the present invention;

FIG. 4 is a reduced side elevational view of the system of FIG. 3 illustrating an aspirator instrument holder in the process of being secured to a mounting surface;

FIG. 5 is a greatly reduced top plan view of the aspirator instrument holder of FIG. 3, illustrating its attachment to a mounting surface;

FIG. 6 is a pictorial view of another cleaning and storage system for a body cavity aspirator instrument which is constructed in accordance with the present invention;

FIG. 7 is a slide elevational view of another cleaning and storage system for a body cavity aspirator instrument which is constructed in accordance with the present invention;

FIG. 8 is a fragmentary pictorial view of another cleaning and storage system for a body cavity aspirator instrument which is constructed in accordance with the present invention; and FIG. 9 is a fragmentary cross sectional view of another aspirator securing arrangement which is constructed in accordance with the present invention.

BEST MODE FOR CARRYING OUT THE INVENTION

Referring now to the drawings, and more particularly to FIGS. 1 and 2 thereof, there is illustrated an aspirator instrument cleaning and storage system 10 which is constructed in accordance with the present invention and which is used with an aspirator 11 and an aspirator instrument 12 to store temporarily the aspirator instrument 12 during periods of temporary non use and to help facilitate the cleaning of the aspirator instrument 12 of residual bodily fluids prior to its use after such temporary storage.

As best seen in FIG. 1, the aspirator 11 is connected via a vacuum tube 14 to a vacuum or suction source having an inlet/outlet fluid connector 15. The aspirator 11 is further connected to the aspirator instrument 12, such as a Yankauer tip instrument 12, via an instrument tube 16.

As best seen in FIG. 2, the Yankauer tip instrument 12 is an elongated generally cylindrically shaped curved hollow tube having an open upper or top end 47 adapted to be secured to the instrument tube 16. The instrument 12 further includes a perforated lower or bottom end 48 having a plurality of spaced apart perforations, such as the perforations 40 and 42 that permits bodily fluids to enter the hollow interior of the instrument 12.

In use, the aspirator 11 is mounted in close proximity to a patient (not shown) and is connected between the instrument 12 and the connector 15 for providing the instrument 12 with a suction or vacuum for fluid removing purposes. In this regard, wherever the patient inserts the instrument 12 into his or her mouth and sucks on the instrument 12, the bodily fluids within the mouth of the patient are drawn into the instrument 12 and through the tube 16 for discharge to the aspirator 11.

As best seen with reference to FIGS. 1 and 2, the cleaning and storage system 10 generally comprises a unitary cylindrically shaped hollow holder 19 having a top open end member 20, a generally U-shaped curved intermediate member 22 which is integrally connected at one of its ends 30 to the top member 20, and a generally cylindrically shaped closed bottom end member 24 integrally connected to an opposite end 32 of the intermediate member 22. The top, intermediate and bottom members 20, 22 and 24 respectively are composed of a moldable plastic material and are configured in combination to a shape that is substantially complementary to a given type of aspirator instrument, such as the Yankauer tip mouthpiece instrument 12. In this regard, the holder 19 is configured to support the aspirator instrument 12 in such a manner to help contain within the holder any residual bodily fluids, such as a mucus fluids, that may remain on and in the instrument 12.

As best seen in FIG. 1, the holder 19 includes an upstanding angularly disposed inlet port 28 which is integrally connected at an upper portion 25 of the bottom member 24. The inlet port 28 is dimensioned for permitting a pipette, a large syringe needle or the like, to be inserted therein for the admitting of a cleaning solution, such as a sodium chloride cleaning solution 17 into the hollow interior of the bottom member 24.

More particularly, for helping to clean the exterior surface and interior passageways of the instrument 12, the cleaning solution 17 is admitted via the port 28, in a sufficient volume to fill the bottom end 24 of the holder 19 with the cleaning solution to about a base level L. In this regard, when the base member 24 is filled with the cleaning solution 17 to the base level L, the distal or lower end 18 of the instrument 12 and its perforations, such as the perforations 40 and 42, are covered completely with the cleaning solution 17. Thus, when the aspirator 11 is activated, the cleaning fluid 17 in the bottom member 24 is drawn from the holder 19 into the instrument 12 and thence, into the aspirator 11 via the tube 16. Thus, any residual bodily fluids in the tip of the instrument 12 will be carried by the cleaning solution 17 and drawn from the instrument 12 cleaning it of the residual mucus fluids for the next subsequent use by the patient/user.

In order to help clean and wipe any residual bodily fluids disposed on the exterior surface of the instrument 12, the system 10 also includes a wiper cap 26 having an elongated slot 58 disposed therein. The cap 26 is dimensioned to be attached removably to the top open end member 20 and is composed of a resilient material that is sufficiently flexible to permit a portion of its surface, to frictionally grip and wipe the exterior surface of the instrument 12 as it passes through the slot 58 as best seen in FIG. 2.

In order to facilitate mounting the holder 19 to a stationary surface, such as a guard bed rail 100, a mounting arrangement 60 (FIG. 1) is integrally connected to the top member 20. The mounting arrangement 60, as will be explained hereinafter in greater detail, is adapted to permit the holder 19 to be secured removably to the guard rail 100 of the bed of a patient. In this manner, the holder 19 can be secured in close proximity to the patient for individual patient use and in close proximity to the aspirator 11 for use by a health care provider when the patient is unable to use the instrument 12 due to his or her physical condition.

Considering now the use of the system 10 with reference to FIGS. 1 and 2, during periods of non-use of the instrument 12, the user initially inserts the instrument 12 into the holder 19 via the slot 58 in slotted wiper cap 26.

In this manner, a portion of the surface area of the wiper cap 26 indicated generally at 27 grips frictionally a portion of the surface walls of the instrument 12 wiping any fluids therefrom onto the cap 26.

As the patient user continues inserting the instrument 12 into the holder 19, the bottom end 48 of the instrument 12 comes into close proximity to about a distal end 21 of the bottom member 24. Thus, once the instrument 12 is fully inserted into the holder 19, the instrument 12 is held securely therein by the cap 26 and is disposed with its perforated bottom end 48 substantially below the inlet port 28. In this manner, when the cleaning solution 17 is admitted to a level L in the bottom member 24 via the inlet 28, the solution 17 is disposed at a sufficient level to clean a substantial portion of the bottom end 48 of the instrument 12.

Thus, to facilitate a thorough and complete cleaning of the base portion 24 of the holder 19 as well as the hollow interior of the instrument 12, a sufficient volume or quantity of the cleaning solution, such as the sodium chloride solution 17, is introduced into the bottom member 24 via the inlet port 28 to completely cover the bottom 48 of the instrument 12. A vacuum is thereafter applied to the instrument 12, to cause the cleaning solution 17 to be drawn from the hollow interior of the bottom portion 24 and into the hollow interior of the instrument 12 for discharged to the aspirator 11.

This cleaning process may be repeated by the user to facilitate and even more thorough and complete cleaning of the instrument 12 and the holder 19.

While a particular embodiment of the present invention has been disclosed, it is to be understood that various different modifications are possible and are contemplated within the true spirit and scope of the appended claims.

For example, different types of materials may be employed in the construction of the holder 19 and such materials may include glass and/or rubber materials. Also, instead of a bent Yankauer mouthpiece configuration, other mouthpiece configurations may be employed for the construction of the holder 19 and such configurations may include a straight mouthpiece configuration, a U-shape mouthpiece configuration and/or a funnel shaped mouthpiece configuration.

Considering now the system 10 in still greater detail with reference to FIGS. 1-2, the inlet port 28 has a unitary construction and is hollow throughout its longitudinal length. An upper port opening 80 defines an entrance to a passageway 98 that extends to a base port opening 86 in the base portion 24. In this regard, the passageway 98 permits the cleaning fluid 17 to be admitted into the base member 24.

Considering now the bottom member 24 in greater detail with reference to FIG. 2, the bottom member 24 is generally cylindrical and has as overall longitudinal length that is substantially longer than the perforated lower end 48 of the instrument 12. In this manner, the hollow interior of the bottom member 24 can be filled with a sufficient volume of the cleaning solution 17 to completely cover the perforated lower end 48 of the instrument 12.

As best seen in FIG. 2, the base member 24 has an elongated tube like cylindrically shaped construction defined by a generally cylindrical wall member 84. The wall member 84 has a sufficient thickness so that it will not be easily broken if accidentally engaged by a syringe or pipette inserted into the inlet 28 and into the hollow interior of the holder 19. The base port opening 86 extends through the wall member 84 for providing access into the hollow interior of the bottom member 24.

Considering now the inlet port 28 in greater detail with reference to FIG. 2, the inlet port 28 is a hollow tubular member which extends angularly upwardly at about an angle $\phi$ between an imaginary line 68 defining the longitudinal axis of the inlet port 28 and an imaginary line 69 defining the longitudinal axis of the top member 20. In this regard, the angle $\phi$ is between about 41 degrees and about 45 degrees. A more preferred angle $\phi$ is between about 42 degrees and about 44 degrees, while the most preferred angle $\phi$ is about 43 degrees.

The inlet port 28 includes a generally circular wall member 80 which is integrally connected to the wall member 84 at a bottom rounded wall member indicated generally at 29 and at a top rounded wall member indicated generally at 33.

The inlet port 28 has an overall longitudinal length this is sufficient to permit the volume of cleaning solution admitted to the hollow interior of the holder 19 to rise above the base port opening 86 to the level L. The level L is a sufficient level to assure the perforated bottom end 48 of the instrument 12 will be emersed in cleaning solution even if the instrument 12 is not fully inserted in the holder 19. For example, as illustrated in FIG. 2, if the instrument 12 is fully inserted into the holder 19 and then slightly withdrawn from the holder, the base port opening 86 will still be disposed substantially above the perforated bottom end 48 of the instrument 12.

Considering now the intermediate member 22 in greater detail with reference to FIGS. 1–2, the intermediate member 22 has a unitary construction and functions to interconnect integrally the top member 20 and the bottom member 24. The intermediate member 22 is generally curved shaped to cause the bottom member 24 to be disposed at about an angle $\theta$ from the vertical relative to the imaginary longitudinal axis 69 of the top member 20. The angle $\theta$ is chosen to enable the perforated bottom end 48 of the instrument 12 to be completely received within the bottom member 24 of the holder 19. In this regard, the angle $\theta$ is between about 12 degrees and about 16 degrees. A more preferred angle $\theta$ is between about 13 degrees and about 15 degrees, while the most preferred angle $\theta$ is about 14 degrees.

The intermediate member 22 includes a generally elongated circular intermediate wall member 72 that has a sufficient inner diameter to permit the instrument 12 to pass through the intermediate member 22 and to be received in the bottom member 24. In this regard, the inner diameter of the intermediate member 22 in combination with its over length is determined by the maximum size of the aspirator instrument 12 to be secured within the device 10. As such mouthpieces have conventional standard sizes, the diameter and length dimensions of the intermediate member 22 are chosen to accommodate such standard sizes.

Considering now the top member 20 in greater detail with reference to FIG. 1, the top member 20 is generally elongated and cylindrical in shape having a unitary construction. A generally upper circular wall member 61 terminates at one of its ends in a lip 63 which defines the mouth 21 into the holder 19. The other end of the wall member 61 is integrally connected to the intermediate wall member 72 and is dimensioned to have the same inner diameter. The longitudinal length of the top member 20 is sufficient for receiving therein a substantial portion of the instrument 12.

Considering now the wiper cap 26 in greater detail with reference to FIG. 2, the wiper cap has a unitary construction and includes a generally circular cap wall member 91 which is integrally connected to a wiper wall member 93. The cap wall member 91 is open at one of its ends 94 and has an inner diameter that is dimensioned to receive therein in a snug friction tight fit an upper neck portion 66 of the top member 20. The other end of the cap wall member 91 is connected integrally to the wiper wall member 93 by a rounded portion 95.

The wiper wall member 93 has a centrally disposed slot 58 which is disposed in a plane perpendicular to the cap wall member 91. The slot 58 includes a pair of spaced apart enlarged openings 96 and 97 (FIG. 1), respectively, disposed at diametrically opposite ends of the slot 58 to provide stress relief on the upper wall member 93 whenever the aspirator instrument 12 is inserted within or removed from the slot 58.

As best seen in FIG. 2, the slot 58 is sufficiently wide to permit the upper wall member 93 to distort and frictionally slide along the wall surface of the instrument 12 as it is being inserted or withdrawn from the holder 19. Thus, the wiper wall member 93 is constructed to engage the instrument 12 in a wiping type action for helping to clean the surface of the instrument 12 from any residual mucus fluids.

Considering now the mounting arrangement 60 in greater detail with reference to FIG. 1, the mounting arrangement 60 generally includes a base plate 102 which is integrally connected to the upper member 24 and opposite and spaced apart from the inlet port 28. A pair of spaced apart resilient clamp members 104 and 106 extend perpendicularly from the base plate 102 and are dimensioned to receive therebetween in a snug friction-tight fit a bed rail, such as the bed rail 100. In this regard, when the clamp members 104 and 106 are brought into simultaneous engagement with the bed rail 100, the clamp member 104 and 106 will cam apart to an open position to receive the rail 100 and then cam close onto the rail 100 in the snug friction tight fit securing removably the holder 19 to the rail 100.

Referring now to the drawings, and more particularly to FIGS. 3–5 thereof, there is shown a cleaning and storage system 310 which is constructed in accordance with the present invention.

The system 310 is substantially similar to system 10 and generally comprises a unitary hollow holder 319 having an open top member 320, a closed bottom end member 324, and an intermediate member 322 which interconnects integrally the top member 320 and the bottom member 324. An integrally connected inlet port 328 is disposed in the bottom member 324. A wiper cap 326 is mounted removably to the holder 319 which is adapted to be secured removably to a stationary surface 13 by a mounting arrangement 360.

The wiper cap 326 generally includes a generally circular cap wall member 391 which has a wiper wall member 393 integrally connected at its top end. The bottom end of the cap wall member 391 defines an opening which is dimensioned for receiving therein in a snug friction tight fit a top portion 320 of the top member 320. The wiper wall member 393 includes a slot 358 which terminate at its diametrically opposite ends in a pair of stress relief holes 396 and 397 respectively.

As the systems 10 and 310 are substantially similar, similarities will not be discussed in greater detail.

Considering now the mounting arrangement 360 in greater detail with reference to FIGS. 3–5, the mounting arrangement 360 generally includes a rectangularly shaped base plate 361 which is integrally connected to the holder 319 at about the top member 320. The base plate 361 is disposed opposite the holder 319 and includes a face 363 having a coat of an adhesive substance 364 disposed thereon.

In order to help facilitate securing the base plate 361 to the mounting surface 300, a rectangularly shaped patch 365 having a plurality of hooks thereon, such as a hook 366, is secured by the adhesive substance 364 to the face 363 of the base plate 361. Another rectangularly shaped patch 372 having a shape corresponding to the path 365 is adapted to be mounted to a stationary wall surface, such as the wall surface 13 in close proximity to the user. The patch 372 includes a front face side with a plurality of piles 373 disposed thereon and an obverse side with an adhesive substance 371 disposed thereon. The adhesive 371 permits the patch 372 to be fixed removably to the stationary surface 13, while the pile 372 are adapted to engage the plurality of holes on the patch 365. In this regard, the patches 365 and 372 are adapted to be secured removably together, thus, permitting the holder 319 to be secured removably to the stationary surface 13.

Referring now to the drawings, and more particularly to FIG. 6 thereof, there is shown a cleaning and storage system 610 which is constructed in accordance with the present invention.

The system 610 is substantially similar to system 10 and includes a holder 619 having an angular displaced inlet port 628 and wiper cap 626. The wiper cap includes a slot 658 having a pair of spaced apart enlarged openings 697 and 698 disposed at diametrically opposite ends of the slot 658 for stress relief purposes. A mounting arrangement 660 permits the holder 619 to be mounted removably to a stationary surface, such as a rail 699 of a bed.

As the system 610 is substantially similar to system 10 except for the mounting arrangement 660, only the mounting arrangement 660 will be described in greater detail.

Considering now the mounting arrangement 660 with reference to FIG. 6, the mounting arrangement 660 includes an adjustable holder clamp 670 having attached therein a spring clamp 680. The adjustable holder clamp 670 is adapted to secure adjustably removably the mounting arrangement 660 to the holder 619, while the spring clamp 680 is adapted to secure removably the mounting arrangement 660 with the holder 619 to a bed rail, such as the bed rail 699.

As best seen in FIG. 6, the holder clamp 670 generally includes an adjustable ring 672 whose diameter is adjustable to accommodate the holder 619. In this regard, the ring 672 includes a rear extension 662 having a thumb nut 664 and bolt 665 disposed therein that permits the diameter of the ring 672 to be adjusted for clamping removably the holder 619 within the ring 672.

The ring 672 also includes a front extension 666 which is adapted to receive therein the spring clamp 680. In this regard, the spring clamp 680 is secured removably to the front extension 666 by a screw 668.

Considering now the spring clamp 680 in greater detail, the spring clamp has a unitary construction and includes a top leaf member 604 and a bottom leaf member 608. The leaf members 604 and 608 are integrally connected in a spaced apart manner by an intermediate/member 609 having a hold 610 therein. The hole 610 is dimensioned for receiving them the screw 668 to permit the spring clamp 680 to be attached removably to the front extension 666.

The leaf members 604 and 606 are biased in such a manner to cause them to grip the rail 699 in a snug friction tight fit for securing removably the holder 619 to the rail 699.

Referring now to the drawings, and more particularly to FIG. 7 thereof, there is shown a cleaning and storage system 710 which is constructed in accordance with the present invention.

The system 710 is substantially similar to system 10 and includes a holder 719 having an angularly disposed inlet port 728 and wiper cap 726. In order to secure removably the holder 719 to a stationary surface, such as the top of a hospital utility stand 780, the system 710 further includes a mounting arrangement 760.

As the system 710 is substantially similar to system 10, except for the mounting arrangement 760, only the mounting arrangement 760 will be described in greater detail.

Considering now the mounting arrangement 760 in greater detail with reference to FIG. 7, the mounting arrangement 760 includes a base plate 762 which is integrally connected to the holder 719 for supporting it in an upright position.

The base plate 762 is generally L shaped having an elongated upper holder support member 763 and an integrally connected lower screw support member 764. The lower screw support member 764 has a thread hole 766 which is adapted for receiving therein threadably a blunt end attachment screw 765 having an enlarged finger engageable head 768.

A space, indicated generally at 769, is formed between the holder 719 and the screw support member 764 and is sufficiently wide to permit a portion of the top of the utility cart 780 to be received therebetween. In this regard, as the screw 765 is rotated in a clockwise direction, it functions to secure the holder 719 to the cart 780.

Referring now to the drawings, and more particularly to FIG. 8 thereof, there is shown a cleaning and storage system 810 which is constructed in accordance with the present invention.

The system 810 is substantially similar to system 10 and includes a holder 810 having an angularly disposed inlet port member 828, wiper cap 826 and mounting arrangement 860. As the system 810 is substantially similar to system 10 except for the mounting arrangement 860, only the mounting arrangement 860 will be described in greater detail.

As best seen in FIG. 8, the mounting arrangement 860 generally includes a pair of spaced apart generally circular tabs 861 and 862. The tabs 861 and 862 are integrally connected to the holder 819 by a pair of tab bar-like support members 863 and 864, respectively, which space the tabs 861 and 862 from the holder 816.

The mounting arrangement 860 also include a tab receiving plate 871 having a pair of spaced apart tab receiving slotted holes 872 and 874, respectively. The slotted holes 872 and 874 are adapted to receive therein the tabs 861 and 862 and their associated support member 863 and 864, respectively. As the slotted holes 872 and 874 are substantially similar only hole 872 will be described in greater detail.

Considering now the slotted hole 872 in greater detail with reference to FIG. 8, the slotted hole 872 generally includes a generally circular opening 880 having a slot 882 disposed at its periphery. The opening 880 is sufficiently large to receive the tab 861 therein, while the slot 882 is sufficiently large to receive the support member 863 therein. In this regard, when the tab 861 and support member 863 are received within the slotted holes 872, the holder 819 is secured or held removable by the plate 871 to a stationary surface (not shown). A mounting screw 890 secures the plate 871 to the stationary surface.

Referring now to the drawings and more particularly to FIG. 9 thereof, there is shown a cleaning and storage system 910 which is constructed in accordance with the present invention.

The system 910 is substantially similar to the system 10 and includes a holder 919, having a top member 920, a bottom member 924 with an angularly disposed inlet port member 828 and an intermediate member 922 for integrally connecting the top member 920 and the bottom member 924 together. A wiper cap 926 is adapted to be disposed on the top member 920, and a mounting arrangement 960 permits the holder 919 to be secured removably to a stationary surface 980. As the system 910 is substantially similar to system 10, except for the mounting arrangement 960, only the mounting arrangement 960 will be described in greater detail.

Considering now the mounting arrangement 960 in greater detail with reference to FIG. 9, the mounting arrangement 960 generally includes a base member 962 having a weight 964 secured thereto by a pair of support posts 988 and 989, respectively. A hole 965 is disposed in the base member 962 and is dimensioned for receiving therein the bottom member 924 forming part of holder 919. In this regard, the holder 919 is secured removably within the base member 962.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. A cleaning and storage system for a body cavity aspirator instrument, comprising:

storage means having a hollow interior for holding temporarily between periods of non-use, the body cavity aspirator instrument;

securing means connected to said storage means for permitting said storage means to be supported removably at a stationary surface; and fluid receiving means connected to said storage means at a base portion thereof for permitting a cleaning fluid to be admitted into the hollow interior of said storage means to help facilitate cleaning the body cavity aspirator instrument prior to its subsequent use.

2. A system according to claim 1, wherein said storage means is elongated tube means configured in a shape substantially complementary to the body cavity aspirator instrument for helping to facilitate its storage in said storage means between periods of non-use.

3. A system according to claim 1, wherein said storage means is elongated tube means having an upper portion and a lower portion, said lower portion being angularly disposed at about an angle θ relative to said upper portion to facilitate the storage of the body cavity aspirator instrument in said storage means; and wherein said securing means is plate means integrally connected to said storage means, said plate means being adapted to be secured removably to said stationary surface.

4. A system according to claim 3, wherein said angle θ is between about 12 degrees and about 16 degrees.

5. A system according to claim 3, wherein said plate means includes:

wall plate means for attachment to the stationary surface; and separable holder plate means integrally connected to said storage means and adapted to be secured removably to said wall plate means for facilitating securing said storage means to said stationary surface.

6. A system according to claim 5, wherein:

said wall plate means includes a front face for engagement with said holder plate means and an obverse face for engagement with the stationary surface; and wherein said wall plate means further includes:

a plurality of piles disposed on said front face to facilitate securing removably the front face of said wall plate means to said holder plate means, and a coating of adhesive on said obverse face to permit the obverse face to be secured to said stationary surface.

7. A system according to claim 6, wherein said holder plate means includes a plurality of hooks for securing removably the plurality of piles disposed on said wall plate means.

8. A system according to claim 3, wherein said fluid receiving means is inlet means integrally connected to said base portion, said inlet means being sufficiently spaced apart from a distal end of said storage means to permit substantially the entire base portion of said storage means to be filled with a fluid to facilitate cleaning of the body cavity aspirator instrument.

9. A system according to claim 8, wherein said inlet means is disposed at about an angle θ relative to an imaginary axis defining the longitudinal axis of said upper portion of said storage means.

10. A system according to claim 9, wherein said angle φ is between about 41 degrees and 45 degrees.

11. A system according to claim 8, further comprising:

wiper cap means secured removably to said upper portion to substantially close said mouth;

said wiper cap means having a resilient wiper surface with means defining an elongated narrow slot disposed therein in substantially parallel alignment with said mouth for permitting the body cavity aspirator instrument to pass therethrough and into said tube means for temporary storage purposes;

said wiper surface engaging flexibly the body cavity aspirator instrument as it is inserted and removed from said tube means for helping to facilitate the removal of surface fluids disposed on the instrument.

12. A system according to claim 1, wherein said securing means for permitting said storage means to be supported removably at said stationary surface is clamp means.

13. A system according to claim 12, wherein said clamp means is integrally connected at a top portion and includes a pair of spaced apart curved shaped resilient gripping members for receiving therebetween a supporting rail to secure the storage means in close proximity to a user.

14. A system according to claim 12, wherein said clamp means includes a ring clamp for removable attachment to said top portion, said ring clamp having a U-shaped resilient gripping member extending perpendicularly therefrom for receiving therein a supporting rail to secure the storage means in close proximity to a user.

15. A system according to claim 12, wherein said clamp means includes an L-shaped base member integrally connected to said bottom member and screw means threadably received within said base member for attaching said base member to a supporting surface.

16. A system according to claim 1, wherein said securing means includes a pair of integrally connected spaced apart supporting tabs;

said supporting tabs being dimensioned to be received within means defining a mounting surface to secure the aspirator securing arrangement in close proximity to a user.

17. A system according to claim 1, wherein said securing means includes:

an elongated upper tube receiving member for receiving the bottom portion of said storage tube means therein in a snug friction tight fit; and base means for supporting from below said elongated tube receiving member in a substantially upright position on a stationary surface.

18. A system according to claim 17, wherein said base means includes weighted base means for helping to prevent the aspirator mouthpiece from unbalancing the securing arrangement when it is stored therein.

* * * * *